United States Patent [19]

Ohkawa et al.

[11] Patent Number: 4,892,099
[45] Date of Patent: Jan. 9, 1990

[54] CATHETER

[75] Inventors: Shin-ichi Ohkawa; Koichi Tsuno; Jun-ichi Hiramoto; Norifumi Matsumiya, all of Konohana, Japan

[73] Assignee: Sumitomo Electric Industries, Ltd., Osaka, Japan

[21] Appl. No.: 284,763

[22] Filed: Dec. 12, 1988

Related U.S. Application Data

[63] Continuation of Ser. No. 41,630, Apr. 22, 1987, abandoned, which is a continuation of Ser. No. 755,468, Jul. 16, 1985, abandoned.

[30] Foreign Application Priority Data

Jul. 18, 1984 [JP] Japan .................. 59-107512[U]
Oct. 4, 1984 [JP] Japan .................. 59-208779

[51] Int. Cl.⁴ .................... A61B 1/06; A61M 29/02
[52] U.S. Cl. .................... 606/194; 128/6; 604/96
[58] Field of Search .................... 128/303.1, 344, 348.1, 128/6, 395; 604/96

[56] References Cited

U.S. PATENT DOCUMENTS

| | | | |
|---|---|---|---|
| 2,247,258 | 6/1941 | Shepard | 128/6 |
| 2,797,683 | 7/1957 | Aiken | 128/398 X |
| 3,100,482 | 8/1963 | Hett | 128/6 |
| 3,467,098 | 9/1969 | Ayres | 128/303.1 |
| 3,724,922 | 4/1973 | Jones | 128/6 X |
| 4,217,891 | 8/1980 | Carson | 128/6 |
| 4,257,420 | 3/1981 | Terayama | 128/303 A |
| 4,392,485 | 7/1983 | Hiltebrandt | 128/6 |
| 4,418,688 | 12/1983 | Loeb | |
| 4,419,987 | 12/1983 | Ogiv | 128/6 X |
| 4,471,766 | 9/1984 | Terayama | 128/6 |
| 4,499,899 | 2/1985 | Lyons | 128/6 |
| 4,576,145 | 3/1986 | Tsuno et al. | 128/6 |

FOREIGN PATENT DOCUMENTS 0080436 6/1983 European Pat. Off. .
8302885 9/1983 World Int. Prop. O. .

OTHER PUBLICATIONS

J. F. Vollmar et al., "Vascular Edoscopy", Surgical Clinics of North American, vol. 54, No. 1, Feb. 1974.
C. A. Athanasavcis, "Percutaneous Transluminal Angioplasty General Principles", Aur:135, Nov. 1980.
P. C. Block, M.D. "Setting Parameters for Percutaneous Transluminal Coronary Angioplasty", Cardvsclr. Med. 1985.
Electronics Letters, vol. 15, No. 25, 12/6/79, pp. 829-830, S. Oikawa et al., "Plastic Optical Fibre with Improved Transmittance".
Patents Abstracts of Japan, vol. 8, No. 38, (P-255), (1475), Feb. 18, 1984, "Endoscope".

Primary Examiner—Michael H. Thaler
Attorney, Agent, or Firm—Cushman, Darby & Cushman

[57] ABSTRACT

A catheter adapted to be inserted into a blood vessel is disclosed which comprises a flexible tube-like sheath including a fluid passage therein and a radially expansive and contractive balloon disposed about the peripheral surface of the distal end portion of said sheath and communicating with said fluid passage. The catheter is characterized in that a light guide formed by extrusion for transmitting illumination light to the leading end of the catheter has disposed therein, an image guide for transmitting an image from the distal end of the catheter, and a transparent liquid guide passage opening at the distal end of the catheter, are guide being disposed substantially in parallel with each other within the flexible tube-like sheath whereby the catheter includes the concurrent function of an endoscope.

7 Claims, 3 Drawing Sheets

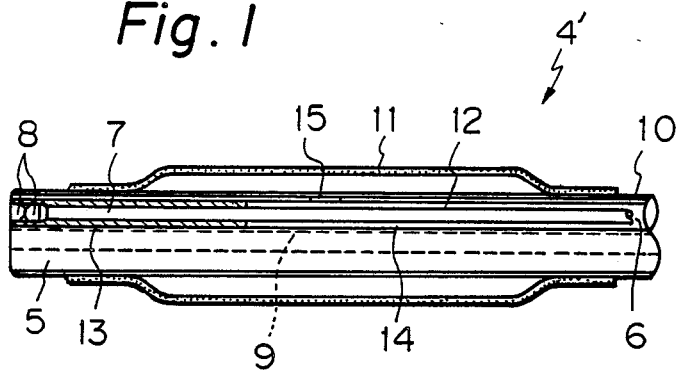
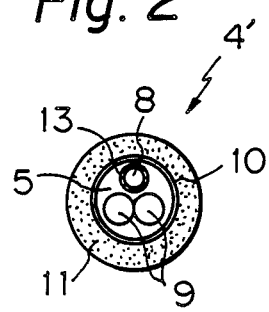
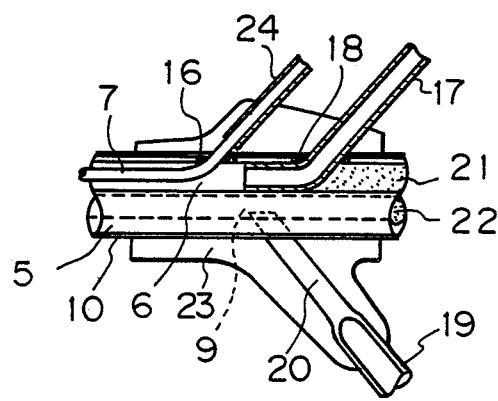
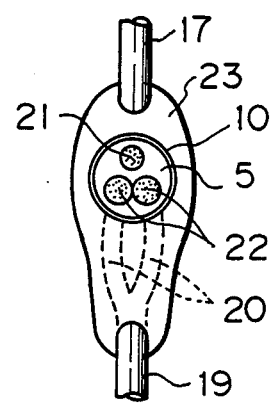

Fig. 9 PRIOR ART
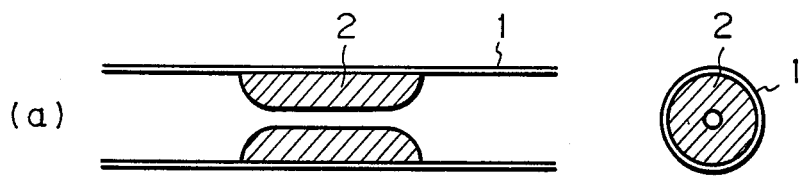
(a)
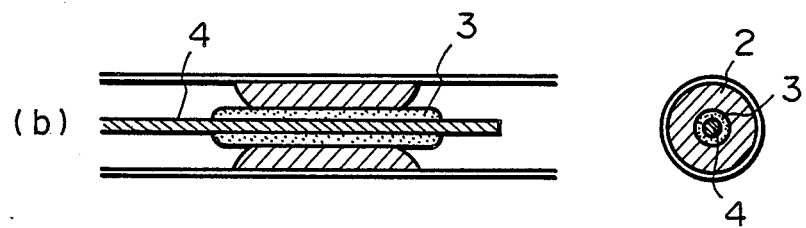
(b)
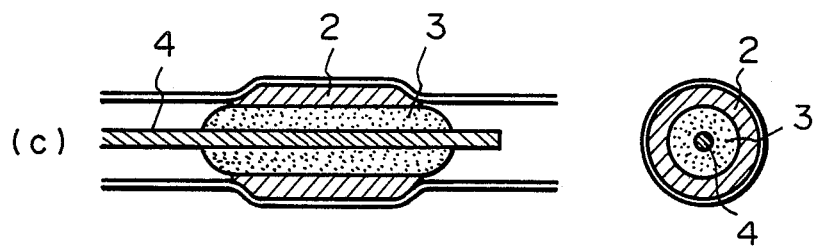
(c)
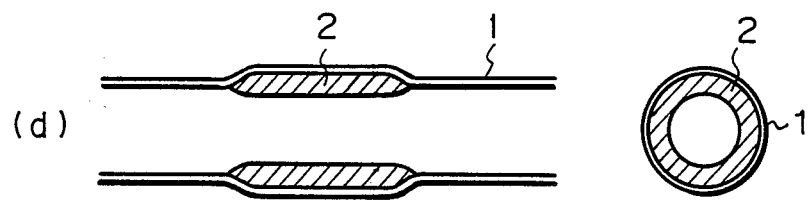
(d)

CATHETER

This is a continuation of application Ser. No. 041,630 filed Apr. 22, 1987, which was abandoned upon the filing hereof, which is a continuation of application Ser. No. 755,468, filed July 16, 1985, which was abandoned.

BACKGROUND OF THE INVENTION

This invention relates to a catheter adapted to be inserted into a blood vessel and, more particularly, to a catheter suitably employed for treatment of heart diseases.

As the conventional medical treatment for ischemic heart diseases such as angina pectoris and myocardial infarctions, the so-called Percutaneous Transluminal Coronary Angioplasty method (abbreviated as "PTCA method" hereinafter) has been known. According to the PTCA method, and as shown in FIGS. 9(a)-(d), a catheter tube 4 having at the distal end an elongated balloon 3 made of polyurethane or the like is inserted into the stenosis 2 formed by a thrombus and cholesterol in the coronary 1, and the balloon is then positioned within the stenosis and expanded radially outwardly to expand the stenosis.

In this method, the location of the stenosis is first detrmined on the basis of a defective area of the shadow image given by an angiography and the balloon is then positioned and expanded.

However, in the above-mentioned PTCA method, since the conditions and nature of the stenosis is judged only from the unclear shadow image of the angiography, the method cannot pinpoint the exact conditions and nature of the stenosis and frequently fails to perform effective treatment. That is, in spite of the fact that other methods such as laser irradiation or injection of thrombus dissolving agent for treatment which depend upon the conditions and nature of the stenosis are appropriate, there are the cases in which effective treatment can not be performed because of the use of the PTCA method. Also, determination made only by means of a shadow image frequently fails to elicit any affirmative confirmation as to whether the balloon is properly positioned with respect to the constriction. Thus, it is said that the probability of the stenosis blocking up again after treatment by the conventional PTCA method is as high as 25-30%.

SUMMARY OF THE INVENTION:

It is therefore a primary object of the present invention to provide a catheter which can pinpoint exactly the conditions and nature of the stenosis to be treated.

According to the present invention, a catheter adapted to be inserted into a blood vessel comprises a flexible tube-like sheath including a fluid passage therein and a radially expansive and contractive balloon disposed about the peripheral surface of the leading end portion of said sheath and communicating with said fluid passage is proposed. A light guide for transmitting illumination light to the distal end of said catheter, an image guide such as an image fiber bundle for transmitting an image from the distal end of said catheter, and a transparent liquid guide passage opening at the distal en of said catheter are disposed substantially parallel to each other within said flexible tube-like sheath, the catheter thereby including the concurrent function of an endoscope.

With the above-mentioned construction and arrangement of the components of the catheter according to the present invention, first of all, the catheter is inserted into a blood vessel while observation is made of a shadow image given by an angiography until the distal end of the catheter is positioned immediately short of the stenosis in the blood vessel. Transparent liquid is then spouted through the flush openings at the distal end of the catheter, and the conditions and nature of the stenosis are observed through the image fiber bundle, the balloon is expanded radially outward to expand the stenosis. After the catheter has been pulled out of the stenosis, it can be confirmed whether the stenosis has been properly expanded or not by observation through the image fiber bundle.

Many other advantages, features and additional objects of the present invention will become apparent to persons skilled in the art upon making reference to the detailed description and the accompanying drawings in which preferred embodiments of the present invention are shown by way of illustrative example. BRIEF DESCRIPTION OF THE DRAWINGS:

FIG. 1 is a longitudinal sectional view of the distal end portion of a first embodiment of the catheter according to the present invention;

FIG. 2 is an end elevational view of the leading end portion of the catheter as shown in FIG. 1;

FIG. 3 is a fragmentary longitudinal sectional view showing the construction of the branching portion of the catheter as shown in FIG. 1;

FIG. 4 is a cross sectional view of said branching portion as shown in FIG. 1;

FIGS. 9a-9d are fragmentary longitudinal sectional views showing the steps of the operation of a conventional catheter according to the PTCA method.

DETAIL DESCRIPTION OF THE PREFERRED EMBODIMENTS

Figure 5:
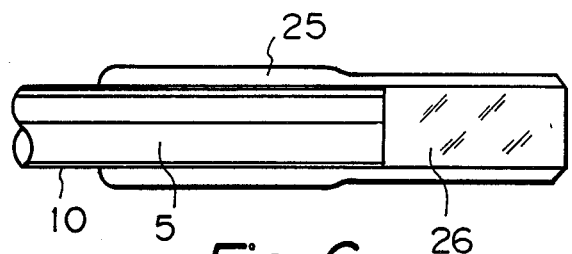
FIG. 5 is a longitudinal sectional view of the rear end portion of the catheter, where the catheter is connected to the light source, as shown in FIG. 1.

The present invention will now be described with reference to the accompanying drawings in which preferred embodiments of the present invention are illustrated. FIGS. 1 and 2 show the construction of the distal end portion of a first embodiment of the catheter 4' according to the present invention. In these Figures, 5 denotes a light guide having a substantially circular cross section for transmitting illumination light therethrough; 6 denotes a through bore formed within the light guide 5 and having its axis substantially parallel to that of the light guide; 7 denotes an image fiber bundle image transmitter disposed within the through bore 6 and provided at the distal end with object lenses 8; 9 denotes transparent liquid guide passages disposed within the light guide 5 and having their axes substantially parallel to those of the light guide and through bore (in the illustrated embodiment, two adjacent passages are provided), said transparent liquid guide passages 9 having flush openings at the distal ends thereof; 10 denotes a flexible radiopaque outer sheath (containing BiC10, BiO or BaSO$_4$) surrounding the light guide 5; and 11 denotes an expansive and contractive balloon provided about the peripheral surface of the distal end portion of the catheter.

The light guide 5 is formed of transparent material such as polymethyl methacrylate, polybutyl methacrylate, copolymer of these materials, polystyrene or polycarbonate. As shown in FIGS. 1 and 2, the light guide 5 is substantially solid within the sections of the catheter except for the portions containing the image fiber bundle 7, through bore 6 and transparent liquid guide passage 9. In fact, the light guide 5 is formed by extrusion so as to include the through bore 6 and transparent liquid guide passages 9 therein. Although not shown, the outer surface of the light guide is provided with a cladding layer.

The outer surface of the image fiber bundle 7 disposed within the through bore 6 is covered by a light shielding coat 12 and the leading end portion of the image fiber bundle 7 and the objective lenses 8 are sealingly fixed to the inner wall of the through bore 6 with a sleeve 13 interposed therebetween. An annular clearance 14 defined between the outer surface of the image fiber bundle 7 and the inner surface of the through bore 6 in a position to the rear of the sleeve 13 provides a fluid passage through which fluid for expanding and contacting the expansive and contractive balloon 11 flows. The fluid passage 14 is in communication with the interior of the balloon 11 through an opening 15 which extends through the light guide 5 and outer sheath 10. The fluid for expanding and contracting the balloon 11 may be a normal saline solution or grape sugar solution. The balloon 11 is formed of polyurethane, polyolefin (e.g. polyethylene, polypropylene, ethylene propylene copolymer etc.) or ethylene vinyl acetate copolymer and when expanded, presents a cylindrical configuration.

FIGS. 3 and 4 show the construction of the branch portion of the above-mentioned embodiment of the catheter. The image fiber bundle 7 is pulled out of the catheter through a through hole 16 formed in the light guide 5 and outer sheath 10 and a tube 17 is inserted at one or the inner end into the through bore 6 with the other or outer end pulled out of the catheter through a through hole 18 formed in the light guide 5 and outer sheath 10. Liquid flows through the tube 17 to expand and contract the balloon 11. the distal end of a second tube 19 for supplying transparent liquid for the purpose of making a flush is bifurcated into two tube branches 20. Each of the tube branches 20 is connected at one end to the associated one of the two transparent liquid guide passages 9 and the other end of each tube branche 20 is then pulled out of the catheter through holes in the same way as stated when referring to tube 17. Each of the through holes through which the image fiber bundle 7 and tubes 17 and 20 are pulled from are then sealed with resin. Also, the portions of the through bore 6 and transparent liquid guide passage 9 positioned rearwardly of the branching portion of the catheter are filled with resin at 21 and 22, respectively. The image fiber bundle and tubes branched in this way are held in position by a split mount 23 provided with grooves for receiving the fiber bundle and tubes, respectively. The exposed portion of the image fiber bundle 7 is covered by a protective coating 24.

FIG. 5 shows the proximal end portion of the embodiment of the catheter described hereinabove. The proximal end portion of the light guide 5 is surrounded by a plug 25 which is adapted to be connected to an illumination light source (not shown). The plug 25 holds a cylindrical glass block 26 or polymethylmethacrylate block having substantially the same diameter as the light guide 5 and in close contact with the proximal end face of the light guide 5 to thereby protect the light guide agaist possible thermal and mechanical damage.

Figure 6:
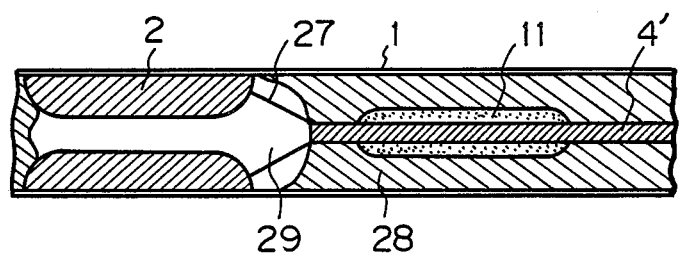
FIG. 6 is a longitudinal sectional view showing the operation of the catheter as shown in FIG. 1.

With the above-mentioned construction and arrangement of the components of the catheter of the invention, as shown in FIG. 6, the catheter 4' is inserted into a blood vessel 1 and is advanced within the blood vessel until the leading end of the catheter reaches a position immediately short of the stenosis 2 of the blood vessel 1 while observation is made of the movement of the catheter through an angiography. Then, transparent flush liquid 27 under pressure is passed through the transparent liquid guide passages 9 to be spouted at the flush openings of the passages whereby the spouted transparent liquid 27 temporarily displaces the blood 28 to form a visual field in front of the catheter. At this time, when the balloon 11 is caused to expand temporarily for interrupting the flow of the blood through the blood vessel 1, the visual field can be easily formed. Under such condition, the illunimation light 29 projected from the leading end of the light guide 5 illuminates the stenosis 2, and it can be observed through the objective lenses 8 and image fiber bundle 7. When it has been found that the conditions and nature of the constriction 2 are suitable for treatment by the PTCA method, the catheter 4' is further advanced into the blood vessel 1 until the balloon 11 is properly positioned with respect to the stenosis 2 whereupon the balloon is expanded radially outward such as to expand the stenosis 2. The positioning of the balloon 11 and the results of the treatment can be similarly observed through the lenses 8 and the image fiber bundle 7.

Figure 7:
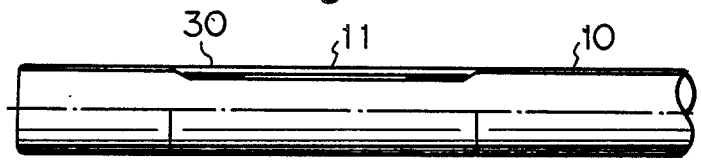
FIG. 7 is a side elevational view of the distal end portion of a second embodiment of the catheter according to the present invention.

FIG. 7 shows another or second embodiment of the catheter according to the present invention. According to the embodiment of FIG. 7, the light guide 5 including the through bore 6 and transparent liquid guide passes 9 therein is first formed by extrusion and, then, the portion 30 of the light guide 5 where the balloon 11 is to be mounted is reduced in outer diameter by thermal deformation. Therefore, when the balloon 11 mounted on the portion 30 contracts, the outer surface of the balloon lies in the plane of the rest of the light guid 5 so that the catheter can be smoothly inserted into the blood vessel 1 and any pain which the patient may feel at the insertion of the catheter into the patient's blood vessel can be alleviated. The construction and arrangement of the other components of the second embodiment are the same as those of the corresponding components of the first embodiment.

Figure 8:
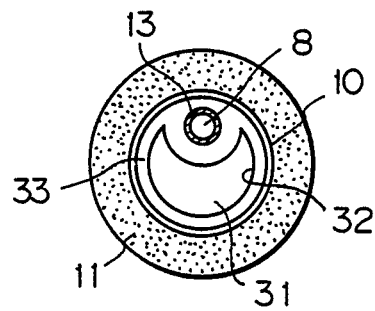
FIG. 8 is a view similar to FIG. 2 but showing a third embodiment of the catheter according to the present invention.

FIG. 8 shows another or third embodiment of the catheter according to the present invention. According to the embodiment of FIG. 8, instead of providing the light guide 5 and the transparent liquid guide passages 9 separately within the section of the catheter as shown in the first embodiment, a singla channel 31 having a reflective inner surface 32 is formed in a material 33 filling the section of the outer tube-like sheath 10; and this single channel 31 serves concurrently as both the light guide and the transparent liquid guide passage. The cross sectional configuration of the channel 31 is semilunar in shape with the concave side thereof facing the image fiber bundle 7 in order to make the section of the channel 31 as large as possible while keeping the outer diameter of the endoscope as small as possible. The reflective inner surface 32 of the channel 31 is formed by a coating of aluminum or gold film vapor-deposition. The illumination light is introduced into the channel 31 through an optical fiber bundle which is sealingly inserted into the channel. By this arrangement, the outer diameter of the endoscope can be made much smaller than that of the first embodiment. If desired, the above stated channel 31 may also be used as a channel for feeding forceps. Namely, there are cases in which an affected part or parts of the interior of the blood vessel not only need to be examined but also need to be cut out. In such cases, the channel 31 may alternatively be used for guiding transparent liquid or feeding forceps. A large cross section of the channel 31 will suffice in preventing any interference with the passage of light through the channel when forceps are also being fed through the channel.

As will be clear from the foregoing description of the preferred embodiments of the present invention, the catheter according to the present invention concurrently functions as an endoscope and, can directly observe the conditions of the stenosis of the blood vessel, which was impossible with the prior art catheters. Thus an appropriate treatment is ensured. Furthermore, since the positioning of the balloon and the post-treatment conditions can be directly observed, the chance of errors occurring in treatment can be substantially reduced. Finally, since a single catheter can concurrently perform both examination and treatment functions, the frequency of the insertion of the catheter into the patient's blood vessel for a particular examination and/or treatment is reduced whereby the pain experienced by the patient can be alleviated accordingly.

What is claimed is:

1. A catheter for insertion into a blood vessel, comprising:
    a flexible tube-like sheath having a fluid passage therein;
    a radially expansive and contractive balloon disposed about the peripheral surface of the distal end portion of said sheath and communicating with said fluid passage;
    a light guide for transmitting illumination light to the distal end of said catheter;
    an image guide for transmitting an image from the distal end of said catheter; and
    a transparent liquid guide having a flush opening at the distal end of said catheter;
    wherein said light guide, said image guide, and said transparent liquid guide are disposed substantially parallel with each other within said flexible tube-like sheath; and
    wherein said light guide comprises a single transparent member formed by extrusion which substantially fills the inside of said flexible tube-like sheath along the entire length of said flexible tube-like sheath such that said image guide and said fluid passage and said transparent liquid guide are also formed with said light guide by extrusion of said single transparent member and disposed within said transparent member.

2. The catheter as set forth in claim 1, in which said light guide is formed of a material selected from the group consisting of polymethyl methacrylate, polymethyl methacrylate copolymer, polybutyl methacrylate, polybutyl methacrylate copolymer, polystyrene and polycarbonate.

3. The catheter as set forth in claim 1, in which said balloon is formed of a material selected from the group consisting of polyurethane, polyolefin and ethylene vinyl acetate copolymer.

4. The catheter as set forth in claim 1, in which said fluid passage is provided by an annular clearance surrounding said image guide bundle within said light guide.

5. The catheter as set forth in claim 1, in which said light guide has at the proximal end a plug to be connected to an illumination light source, said plug including a cylindrical block disposed therein which is in close contact with the proximal end face of said light guide and has substantially the same diameter as said light guide.

6. The catheter as set forth in claim 5, in which said cylindrical block is made of glass.

7. The catheter as set forth in claim 5, in which said cylindrical block is made of polymethyl methacrylate.

* * * * *